United States Patent [19]

Bernard et al.

[11] 4,061,690
[45] Dec. 6, 1977

[54] METHOD OF CATALYTIC CONVERSION OF BUTANE

[75] Inventors: Jean-René Bernard, Saint-Symphorien; Jacques Bousquet, Irigny; Michel Grand, Saint-Symphorien, all of France

[73] Assignee: Societe Nationale Elf Aquitaine, Courbevoie, France

[21] Appl. No.: 694,434

[22] Filed: June 9, 1976

[30] Foreign Application Priority Data

June 17, 1975 France .................................. 75.18911

[51] Int. Cl.$^2$ .............................................. C07C 3/42
[52] U.S. Cl. ................................. 260/676 R; 208/111
[58] Field of Search ...................... 260/676 R; 208/111

[56] References Cited

U.S. PATENT DOCUMENTS

| 3,442,795 | 5/1969 | Kerr et al. | 208/120 |
| 3,480,539 | 11/1969 | Voorhies et al. | 208/111 |
| 3,551,353 | 12/1970 | Chen et al. | 208/111 |

*Primary Examiner*—C. Davis
*Attorney, Agent, or Firm*—Cushman, Darby & Cushman

[57] ABSTRACT

In a method of catalytic conversion of a butane cut to propane, a butane cut and hydrogen are introduced respectively into a reaction zone containing a catalyst consisting of mordenite in acid form in such a manner as to ensure that the partial pressure of hydrogen is higher than 5 bar.

16 Claims, No Drawings

METHOD OF CATALYTIC CONVERSION OF BUTANE

This invention relates to a method of conversion of butane to propane. In more exact terms, the method according to the invention permits the conversion to propane of a butane cut by cracking of the charge in the presence of hydrogen and of a catalyst consisting of acid mordenite.

Although many documents describing cracking or hydrocracking of hydrocarbon charges are to be found in the relevant literature, these documents mostly deal with the conversion of liquid hydrocarbons and much more rarely with the conversion of gaseous hydrocarbons. Gaseous hydrocarbons are naturally understood to mean those which are under normal conditions of temperature and pressure and have a number of carbon atoms per molecule which is either equal to or less than four.

The few patents and publications which deal with this subject, especially those which are concerned with cracking of butane can be considered to fall into two classes: on the one hand those which describe catalytic cracking of the charge and on the other hand those which describe hydrocracking of the charge (also a catalytic process).

The documents of the first class show that the "simple" cracking process is carried out by means of a monofunctional acid catalyst of the silica-alumina type. The documents of the second class illustrate the use for hydrocracking of butane of bifunctional catalysts, that is, of catalysts which have a cracking function by virtue of their acidic properties and a hydrogenation-dehydrogenation function. These latter catalysts usually consist of an acid support which is similar to the catalysts employed for catalytic cracking of the silica-alumina type which is endowed with a hydrogenating activity by introducing a metal of group VIII of the Periodic Table of Elements.

Among the acid compounds which are most frequently employed as catalysts in this type of process, mention can be made of the natural or synthetic crystalline alumino-silicates such as the X, Y zeolites and so forth.

If a hydrocarbon conversion process is to prove advantageous on an industrial scale, it must necessarily satisfy a certain number of criteria:
 a good overall level of conversion of the feedstock
 selectivity of the catalytic conversion process
 stability of the catalyst employed, thus permitting high efficiencies.

The techniques which have been proposed up to the present time for the conversion of butane to propane are not satisfactory from an industrial standpoint by reason of the fact that the conversion yields are mostly insufficient. This is essentially due to the nature of the catalyst. In fact, since the charges which are processed industrially are constituted by a mixture of n-butane and iso-butane, certain catalysts are not well suited and convert only the n-paraffins of the charge without reaching the iso-paraffins. In the case of other catalysts which are capable of converting iso-butane and n-butane, the operating conditions do not make it possible to achieve a sufficient degree of conversion, selectivity and stability.

The aim of the present invention is to propose an industrial process for the conversion of butane to propane which is capable of converting the entire charge, that is to say both iso-butane and n-butane under conditions of operation which permit high efficiencies.

The invention is directed to a method of catalytic conversion of a butane cut to propane, wherein said method consists in introducing into a reaction zone containing a catalyst consisting of acid mordenite on the one hand a butane cut and on the other hand hydrogen so that the partial hydrogen pressure is higher than 5 bar.

It has in fact been found — and this is one of the surprising points of the invention — that in the entire family of alumino-silicates, acid mordenite could be employed as hydroconversion catalyst of the n and iso-butanes to propane without entailing any need to add a hydrogenating metal thereto provided only that the partial hydrogen pressure is sufficient. Furthermore, in contrast to many alumino-silicates, acid mordenite permits conversion of both iso-butane and of n-butane to an equal extent.

The catalyst in accordance with the invention, namely acid mordenite, is a well known alumino-silicate or zeolite, the description of which can be found in the book by D. W. Breck entitled "Zeolite Molecular Sieve", published by Wiley & Sons.

The chemical composition of mordenite related to one cellular unit can be represented by the formula:

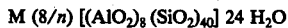

$$M_{(8/n)} [(AlO_2)_8 (SiO_2)_{40}] \; 24 \; H_2O$$

where M is a cation having a valence n.

As in the case of all zeolites, mordenite is a crystalline silico-aluminate constituted by $SiO_4$ and $AlO_4^-$ tetrahedron groups, the negative charge being compensated by an exchangeable cation. Mordenite occurs in the natural state in the form of a salt of sodium, calcium and/or potassium. In the method according to the invention, mordenite is employed in its acid form by replacing the cation which is present by the hydrogen ion or a plurivalent cation. By way of example, this replacement can be achieved by ion exchange with said cation or the ammonium ion for the hydrogen form followed by drying and calcination of the zeolite. The plurivalent cations which endow the mordenite with acidity and therefore hydrocracking activity are the alkaline-earth cations such as beryllium, magnesium, calcium, strontium and barium or else the cations of the rare earths. However, it is preferable to employ mordenite in its hydrogen form by virtue of its higher activity, with a residual proportion of sodium of less than 1% by weight with respect to the dehydrated mordenite.

Two types of mordenite in fact occur, namely the large-pore mordenites and the small-pore mordenites. By way of indication, the mordenites in the form of sodium are capable of sorbing hydrocarbons having a diameter of less than approximately 7 A in the case of the large-pore mordenites and approximately 5 A in the case of the small-pore mordenites. If the mordenite is in its hydrogen form, the size of the sorbed molecules can increase to 8 – 9 A in the case of the large-pore varieties and 7 A in the case of the small-pore varieties.

It should be noted that mordenite is not completely characterized by the formula given above since it can be modified by selective dissolution of alumina by means of suitable solvents such as mineral acids. The best characterization of mordenites is their X-ray diffraction diagram which is the same in the case of all the mordenites. A characteristic diagram of mordenite is given in the book by D. W. Breck cited earlier, on pages 231, 363 and 364.

It is sometimes also an advantage to employ a de-aluminated mordenite in the method in accordance with the invention. In fact, the de-alumination treatment often confers better activity and especially higher stability on the catalyst in the hydrocracking processes. It can be considered that a mordenite is really de-aluminated when the silicon/aluminum molar ratio is equal to or higher than 10. By way of indication, the de-alumination treatment can be performed as follows: the mordenite is treated at the boiling-point for a period of a few hours with a twice-normal hydrochloric acid solution, whereupon the solid is filtered, washed and finally dried. An analysis by X-ray diffraction shows that said solid exhibits the characteristic diagram of mordenite.

One of the essential characteristics of the invention lies in the fact that catalytic cracking of butane to propane is carried out in the presence of hydrogen. In order to ensure that the method secures all the advantages of the invention, especially from the point of view of stability, it is essential to ensure that the partial hydrogen pressure in the reaction zone is of a high order, that is, within the range of 5 to 100 bar. The partial hydrogen pressure is usually within the range of 20 to 80 bar and preferably between 20 and 40 bar.

The method according to the invention can be carried out over a wide temperature range, for example between 250° and 550° C, and more precisely between 325° and 450° C.

The total pressure existing in the reaction zone depends on the one hand on the quantity of hydrogen introduced and therefore on its partial pressure but also on the quantity of hydrocarbon charge injected. The ratio between the quantities of hydrogen and hydrocarbons injected is usually expressed in moles and is conventionally represented by the ratio $H_2/HC$. This ratio $H_2/HC$ usually ranges from 1 to 20 and more advantageously from 2 to 8.

The rate of injection of butanes is represented by the spatial velocity of introduction of the hydrocarbon charge in liquid form: VVH is the hourly volume rate of flow of charge per volume of catalyst. The value of VVH ranges from 0.1 to 10 and more especially from 0.5 to 5 $h^{-1}$.

A further advantage of the catalyst in accordance with the invention is that it can readily be regenerated either by controlled combustion at atmospheric pressure or by treatment with hydrogen at high temperature: 500° C.

A more complete understanding of the invention will be obtained in the light of the following examples which are given without any limitation being implied. These examples can be considered to fall in two classes, namely those performed at atmospheric pressure which serve to select the catalysts and those performed under pressure which illustrate the method according to the invention from an industrial viewpoint.

In the following examples 1 to 10, 1 gram of catalyst is placed in a glass reaction vessel which operates at atmospheric pressure and is pre-treated in hydrogen at 450° C for a period of 16 hours. There is then fed into the reaction vessel a gaseous mixture of hydrogen and butane with a volume ratio $H_2/C_4$ of 7 to 8 at a total gas VVH of 400 $h^{-1}$, this definition of spatial velocity being specific to tests at atmospheric pressure. The activity is given by the temperature of the reaction and the level of conversion to products which are lighter than butane; the selectivity ($^SC_3$) is given by the molar ratio:

$$(^SC_3) = 200\ C_3/(C_1 + C_2 + C_3)$$

wherein $C_1$, $C_2$, $C_3$ represent the molar percentages of methane, ethane and propane in the effluents. From the point of view of selectivity, a valve of 100 in respect of $^SC_3$ corresponds to perfect stoichiometry so that 1 mole of butane yields 1 mole of propane plus 1 mole of methane and a value of 200 in respect of $^SC_3$ shows that the sole product of the cracking process is propane.

EXAMPLES 1 and 2

The catalyst employed is a large-pore mordenite exchanged by protons (Zeolon H). The weight analysis of the catalyst is as follows:

Si : 40.6%; Al : 6.2%; Na : 0.2%.

The treated feedstock is $n$-butane in Example 1 and iso-butane in Example 2. The results obtained are as follows:

EXAMPLE 1: at 330° C and after 1 hour of operation of the catalyst, the conversion is 41% and the value of selectivity $^SC_3$ is 198.

EXAMPLE 2: at 310° C and after 1 hour of operation of the catalyst, the conversion is 24% and the value of selectivity $^SC_3$ is 199.

As may be noted from the foregoing, the results obtained with $n$-butane and iso-butane are of the same order both in regard to activity and in regard to selectivity.

In contrast to other hydrocracking catalysts, the catalyst in accordance with the invention does not produce a simple breakdown of the butane into two lighter hydrocarbons but essentially produces propane since the value of $^SC_3$ is close to 200.

There is noted in both cases the appearance of iso-butane or of $n$-butane, of $n$-pentane and of iso-pentane which disappear when the conversion is brought to a higher level by increasing the temperature. After four hours of operation of the catalyst, an appreciable de-activation is noted since the conversion is then 19% in the case of Example 1 and 12% in the case of Example 2. The catalysts are therefore not stable since they are employed at atmospheric pressure even in the presence of hydrogen.

EXAMPLE 3

The catalyst employed is the large-pore mordenite of Examples 1 and 2 exchanged by calcium ions. The catalyst contains 6.3% by weight of calcium. In the case of an $n$-butane feedstock and under the conditions of Example 1, the conversion after 1 hour of operation of the catalyst is 15% and the selectivity $^SC_3$ is 162.

EXAMPLES 4 and 5

These examples which do not form part of the invention illustrate the use of a conventional zeolite, namely erionite, in the method according to the invention. In these examples, the mordenite of Examples 1 and 2 is therefore replaced by 1 gram of natural erionite exchanged three times by a 5% ammonium chloride solution. Prior to utilization, the erionite is pre-treated with hydrogen as indicated in the foregoing.

The results obtained are as follows:

EXAMPLE 4 ($n$-butane feedstock): at 400° C, the conversion is 23% and the selectivity $^SC_3$ is 182.

EXAMPLE 5 (iso-butane feedstock): under the same conditions, the conversion is zero irrespective of the temperature.

These results show that the erionite is a less active catalyst than mordenite since, at a higher temperature of 400° C instead of 330° C, the conversion of n-butane is lower, namely 23% instead of 41%. They even show that erionite converts less n-butane than mordenite converts iso-butane since, in order to attain the same conversion, namely 23 – 24%, it is necessary to operate at a much higher temperature, namely 400° C instead of 310° C.

Finally, these results show that erionite is absolutely incapable of converting iso-butane.

EXAMPLES 6 and 7

These examples are intended to illustrate the importance of the function of hydrogen in the method according to the invention.

In these examples, the catalyst of Example 1 is utilized at a temperature of 290° C with a feedstock consisting of n-butane, the conditions of flow being those described above. However, in Example 7, hydrogen is replaced by helium.

The results obtained are as follows:

| Operating time (min) | 160 min | 320 min |
|---|---|---|
| Conversion in the presence of hydrogen | 32% | 24% |
| Conversion in the presence of helium | 20.2% | 5.4% |

As can be observed, the conversion obtained is much higher in the presence of hydrogen (32%) than in the presence of helium (20.2%); in addition, the catalyst employed with hydrogen is much more stable: 24% conversion after 5 hours instead of 5% approximately with helium. It should be noted that these results have been obtained without entailing any need to incorporate a hydrogenating metal with the zeolite.

EXAMPLE 8

20 g of mordenite employed in Example 1 are processed for 8 hours by a boiling solution of 2 N hydrochloric acid. The product is filtered, washed and dried at 120° C. Analysis by X-ray diffraction shows that this product is again mordenite which is well crystallized. The weight analysis is as follows:

Si, 42.2%; Al, 3.8%; Na, 0.05%.

The catalyst is tested under the conditions described in Example 1 with n-butane. At 290° C, after 160 minutes of operation, the conversion is 41% and the selectivity is 199.

The results obtained show that de-alumination of the mordenite increases the activity of the catalyst for cracking butane. The temperature is lower by 20° C than that of Example 1 for the same value of conversion and the same selectivity. Moreover, the stability of the catalyst is improved.

EXAMPLE 9

A commercial small-pore mordenite exchanged by ammonium cations (Alite 180) is calcined for a period of 16 hours at 450° C in order to convert it to the hydrogenated form. The mordenite contains 38.2% Si and 8.0% Al. It is then tested on n-butane under the conditions of Example 1. After 160 minutes of operation, the conversion of the n-butane at 340° C is 14% and the selectivity is 185.

EXAMPLE 10

20 grams of the small-pore mordenite employed in Example 9 are treated at boiling point for a period of 8 hours with a 2 N hydrochloric acid solution. After filtration, washing and drying, the product exhibits the characteristic lines of mordenite in X-ray diffraction and contains 39.5% Si and 6.7% Al.

The product is then tested as catalyst under the conditions described in Example 1. After 160 minutes of operation, the conversion of n-butane at 340° C is 36.6% and the selectivity is 190.

EXAMPLE 11

A feedstock consisting of a mixture of n-butane (60%) and iso-butane (40%) is treated by means of a catalyst consisting of acid mordenite in the presence of hydrogen (catalyst of Example 1).

The operating conditions are as follows:

Total pressure: 30 bar; $H_2/HC$: 6; liquid VVH : 0.8 $h^{-1}$; temperature : 400° C.

The hydrocarbon effluent derived from the reaction vessel has the following composition:

Methane, 7.0%; ethane, 10.0%; propane, 75.0%; iso-butane, 3.4%; n-butane, 4.3%; pentane, 0.3%.

Conversion is therefore 92% and the propane yield is 75%, which corresponds to a selectivity $SC_3$ of approximately 140.

By way of indication, a feedstock of n-butane treated with a catalyst essentially consisting of erionite under the following conditions:

Total pressure of 21 bar; $H_2/HC = 12$; VVH = 1.5 $h^{-1}$ and temperature equals 500° C produces 64% propane at a conversion rate of 93%.

If an n-butane/iso-butane mixture at 60%/40% is treated under the same conditions (with an erionite catalyst), the conversion obtained is approximately 56% and the propane yield is 38%.

EXAMPLE 12

In this example, the treated feedstock is a mixture of 61%/39% of n-butane and iso-butane and the catalyst is similar to that of Example 1.

The operating conditions are as follows:

Total pressure: 30 bar; $H_2/HC = 3$; VVH = 0.8 $h^{-1}$; Temperature: 400° C.

After 1000 hours of operation, the reaction products are distributed as follows in respect of a conversion of 87.6%:

| methane | 5.5 % | ethane | 8.8 % | propane | 72.15 % |
|---|---|---|---|---|---|
| iso-butane | 5.2 % | n-butane | 7.2 % | iso-pentane | 0.75 % |
|  |  |  |  | n-pentane | 0.40 % |

EXAMPLE 13

Example 12 is repeated by replacing hydrogen by helium (partial pressure of 22.5 bar). The results obtained are as follows (as a function of the time-duration, the percentages being percentages by weight).

| Operating times | 1 h 30 | 3 h | 5 h | 10 h | 15 h | 20 h |
|---|---|---|---|---|---|---|
| Conversion | 18.78 | 6.79 | 5.56 | 1.45 | 0.88 | 0.63 |
| Methane | 0.80 | 0.36 | 0.19 | 0.06 | — | — |
| Ethane | 1.10 | 0.46 | 0.21 | 0.06 | — | — |
| Propane | 16.60 | 5.97 | 3.16 | 1.33 | 0.88 | 0.63 |
| Iso-butane | 43.49 | 47.83 | 47.75 | 49.71 | 49.22 | 49.44 |

| -continued | | | | | | |
|---|---|---|---|---|---|---|
| Operating times | 1 h 30 | 3 h | 5 h | 10 h | 15 h | 20 h |
| Conversion | 18.78 | 6.79 | 5.56 | 1.45 | 0.88 | 0.63 |
| n-butane | 38.11 | 45.38 | 48.69 | 48.84 | 49.90 | 49.93 |

As can be observed the catalyst initially has a very low activity which decreases even further as soon as the operating time exceeds a few hours.

Hydrogen is therefore essential to good operation of the process. As has been noted earlier, it is also essential to ensure that the quantity of hydrogen which is present is such that its partial pressure is higher than 10 or preferably higher than 15 bar in order to ensure sufficient stability of the catalytic system.

EXAMPLE 14

The catalysts of the invention are stable for a period of several months under the conditions of Example 11. However, the presence of impurities such as olefins are liable to de-activate the catalyst. By way of example, the performances of a catalyst which has been de-activated by a cut $C_4$ containing 90% of butenes are:

Pressure : 30 bar; $H_2$/HC : 6; VVH : 0.8 $h^{-1}$; temperature 400° C; conversion : 7.4%; propane yield (weight %) : 4.3%.

In order to regenerate this catalyst, it is subjected to controlled combustion at atmospheric pressure in an atmosphere of nitrogen plus oxygen containing 3 volume % of oxygen. The treatment is carried out at a temperature of 450° C and lasts 6 hours.

After regeneration, the performances of the catalyst are as follows, under the same operating conditions as above:

Conversion: 86%; propane yield (weight %): 73.3%.

What we claim is:

1. A method of catalytic conversion of a butane cut to propane, wherein said method consists in introducing into a reaction zone containing a catalyst consisting of acid mordenite on the one hand a butane cut and on the other hand hydrogen so that the partial hydrogen pressure is higher than 5 bar.

2. A method according to claim 1, wherein the mordenite is in its hydrogen form.

3. A method according to claim 1, wherein the exchangeable cations of the mordenite are selected from the alkaline earths and/or the rare earths.

4. A method according to claim 1, wherein the mordenite employed has a silicon/aluminum ratio which is higher than 10.

5. A method according to claim 4, wherein the mordenite employed has been obtained by de-alumination of a conventional mordenite by means of acid solvents.

6. A method according to claim 1, wherein the temperature of operation is within the range of 250° to 550° C.

7. A method according to claim 1, wherein the partial hydrogen pressure is within the range of 20 to 80 bar.

8. A method according to claim 1, wherein the hydrogen/butane molar ratio is within the range of 2 to 20.

9. A method according to claim 1, wherein the spatial rate of introduction of the feedstock in liquid form is within the range of 0.1 to 10 $h^{-1}$.

10. A method according to claim 1, wherein the partial hydrogen pressure is within the range of 5 to 100 bar.

11. A method according to claim 6, wherein the temperature of operation is within the range of 325° to 450° C.

12. A method according to claim 7, wherein the partial hydrogen pressure is within the range of 20 to 40 bar.

13. A method according to claim 8 wherein the hydrogen/butane molar ratio is within the range of 2 to 8.

14. A method according to claim 9 wherein the spatial rate of introduction of the feedstock in liquid form is within the range of 0.5 to 5 $h^{-1}$.

15. A method of catalytically converting $n$ and isobutanes into propane comprising introducing the butane cut feedstock in liquid form at a spatial rate within the range of 0.1 to 10 $h^{-1}$ into a reaction zone containing as catalyst an acid mordenite and having a partial hydrogen pressure of between 5 and 100 bar, the hydrogen/butane molar ratio is in the range of 2 to 20, said conversion conducted at a temperature within the range of 250° to 550° C, thereby catalytically converting said butane cut to propane.

16. In a catalytic process for converting a butane cut into propane, the improvement comprising contacting said butane cut with an acid mordenite catalyst in the presence of a partial hydrogen pressure of 20 to 80 bar in a reaction zone at a temperature of about 325° to 450° C, said process characterized by:
 a hydrogen/butane molar ratio within the range of 2 to 8, and
 a spatial rate of liquid butane feedstock introduction with the range of 0.5 to 5 $h^{-1}$, thereby resulting in improved propane yields and avoiding the use of a hydrogenating metal.

* * * * *